US009330299B2

(12) United States Patent
Makihira

(10) Patent No.: US 9,330,299 B2
(45) Date of Patent: May 3, 2016

(54) FUNDUS IMAGE ACQUIRING APPARATUS AND CONTROL METHOD THEREFOR

(75) Inventor: Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 572 days.

(21) Appl. No.: 13/701,062

(22) PCT Filed: Jun. 7, 2011

(86) PCT No.: PCT/JP2011/063441
§ 371 (c)(1),
(2), (4) Date: Nov. 30, 2012

(87) PCT Pub. No.: WO2011/158766
PCT Pub. Date: Dec. 22, 2011

(65) Prior Publication Data
US 2013/0070988 A1    Mar. 21, 2013

(30) Foreign Application Priority Data

Jun. 17, 2010   (JP) ................. 2010-137945

(51) Int. Cl.
*G06K 9/00* (2006.01)
*A61B 3/00* (2006.01)
*A61B 3/14* (2006.01)

(52) U.S. Cl.
CPC .......... *G06K 9/00281* (2013.01); *A61B 3/0025* (2013.01); *A61B 3/14* (2013.01)

(58) Field of Classification Search
CPC ................... G06T 5/007; G06T 5/009; G06T 2207/10144; G06T 2207/10141; G06T 2207/10148; G06T 2207/10152; H04N 1/407; H04N 1/4072; H04N 1/4074; H04N 5/2355; H04N 5/2176
See application file for complete search history.

(56) References Cited

U.S. PATENT DOCUMENTS 6,301,440 B1 * 10/2001 Bolle ................. G06K 9/00664
348/229.1
6,512,837 B1 * 1/2003 Ahmed ................. G06T 1/0028
382/100

(Continued)

FOREIGN PATENT DOCUMENTS

EP       2 184 004 A1    5/2010
JP    2000-201289 A      7/2000

(Continued)

OTHER PUBLICATIONS

Dec. 19, 2012 International Preliminary Report on Patentability in International Patent Appln. No. PCT/JP2011/063441.

(Continued)

*Primary Examiner* — Avinash Yentrapati
(74) *Attorney, Agent, or Firm* — Fitzpatrick, Cella, Harper & Scinto

(57) ABSTRACT

Provided is a fundus image acquiring apparatus in which eyeball tracking can be performed by template matching even if sufficient luminance of a characteristic image of blood vessels or the like is not secured in a case where eye movement is detected accurately from a fundus image. The fundus image acquiring apparatus includes a fundus imaging unit for obtaining a fundus image, an extraction unit for extracting a characteristic image from an initial fundus image taken by the fundus image acquiring apparatus, an evaluation unit for evaluating luminance information of a characteristic point obtained through the extraction, and a setting unit for setting a frame rate for imaging by the fundus image acquiring apparatus. The frame rate is determined based on a result of the evaluation by the evaluation unit.

13 Claims, 13 Drawing Sheets

(56) References Cited

U.S. PATENT DOCUMENTS

| | | | |
|---|---|---|---|
| 6,999,118 B2* | 2/2006 | Suzuki | H04N 5/235 348/226.1 |
| 7,440,593 B1* | 10/2008 | Steinberg | G06K 9/00228 348/207.99 |
| 7,568,800 B2 | 8/2009 | Mihashi et al. | |
| 7,868,915 B2* | 1/2011 | Izawa | G06K 9/00248 348/169 |
| 8,494,286 B2* | 7/2013 | Capata | G06K 9/00228 382/103 |
| 2002/0089643 A1 | 7/2002 | Ogawa | |
| 2005/0270486 A1* | 12/2005 | Teiwes | A61B 3/113 351/209 |
| 2005/0281440 A1 | 12/2005 | Pemer | |
| 2007/0002276 A1 | 1/2007 | Hirohara et al. | |
| 2007/0081721 A1* | 4/2007 | Xiao | G06T 5/009 382/167 |
| 2008/0007691 A1* | 1/2008 | Mihashi | G06T 7/0028 351/206 |
| 2008/0024721 A1 | 1/2008 | Ueno et al. | |
| 2008/0075322 A1* | 3/2008 | Dube | G06K 9/00134 382/100 |
| 2008/0259275 A1 | 10/2008 | Aoki et al. | |
| 2009/0003652 A1* | 1/2009 | Steinberg | G06K 9/00228 382/103 |
| 2009/0244329 A1* | 10/2009 | Kuniba | G06T 5/009 348/241 |
| 2009/0251534 A1* | 10/2009 | Fujimoto | B60R 11/04 348/78 |
| 2010/0329561 A1* | 12/2010 | Sakai | G06K 9/00664 382/173 |
| 2011/0230751 A1* | 9/2011 | Kersting | A61F 9/00736 600/407 |
| 2011/0267580 A1* | 11/2011 | Nakajima | G06K 9/00597 351/206 |
| 2011/0304820 A1* | 12/2011 | Falt | G06T 5/50 351/206 |
| 2012/0002166 A1* | 1/2012 | Tomatsu | A61B 3/0025 351/208 |
| 2012/0154747 A1* | 6/2012 | Makihira | A61B 3/10 351/206 |
| 2012/0229761 A1 | 9/2012 | Makihira | |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2012/0327365 A1 | 12/2012 | Makihira | |

FOREIGN PATENT DOCUMENTS

| | | |
|---|---|---|
| JP | 2001-070247 A | 3/2001 |
| JP | 2007-330558 A | 12/2007 |
| JP | 2008-029467 A | 2/2008 |

OTHER PUBLICATIONS

Oct. 6, 2011 International Search Report and Written Opinion in International Patent Appln. No. PCT/JP2011/063441.

Apr. 1, 2015 Chinese Official Action in Chinese Patent Appln. No. 201180029929.1.

* cited by examiner

FUNDUS IMAGE ACQUIRING APPARATUS AND CONTROL METHOD THEREFOR

TECHNICAL FIELD

The present invention relates to a fundus image acquiring apparatus and a control method therefor. In particular, the present invention relates to a fundus image acquiring apparatus for measuring eye movement, and a control method therefor.

BACKGROUND ART

In recent years, an apparatus for measuring eye movement has received attention. If the eye movement can be measured, such technology is applied to a vision field test or a fundus tomographic image acquiring apparatus for obtaining a higher resolution image, and hence a more accurate fundus test can be performed.

In order to measure the eye movement, there are various methods such as a corneal reflex method (Purkinje image) and a search coil method. Among others, a method of measuring eye movement from a fundus image is being studied, which is simple and imposes little load on a subject.

In order to measure eye movement accurately using a fundus image, it is necessary to extract a characteristic point from the fundus image, to search for and detect a characteristic point in the image to be processed, and then to calculate a movement amount of the characteristic point. These steps need to be processed at high speed. The step of extracting the characteristic point is important from a viewpoint of measurement stability, accuracy, and reproducibility of eye movement. As the characteristic point of the fundus image, a macula lutea, an optic papilla (hereinafter referred to as papilla), or the like is used. Because an affected eye or the like has an incomplete macula lutea or papilla in many cases, a blood vessel may be used as the characteristic point of the fundus image. A method of extracting a characteristic point of a blood vessel is disclosed in Patent Literature 1.

CITATION LIST

Patent Literature

PTL 1: Japanese Patent Application Laid-Open No. 2001-70247

SUMMARY OF INVENTION

Technical Problem

In order to detect eye movement accurately from a fundus image, the method as described in Patent Literature 1 is used for extracting a characteristic point of the fundus, and images are compared so that an eye movement amount between the obtained images can be calculated.

However, if luminance of the characteristic point such as a blood vessel cannot be secured sufficiently, there is a problem that it takes time to extract the characteristic point or that the extraction is failed, and hence tracking cannot be performed.

Therefore, an object of the present invention is to obtain fundus images having sufficient luminance for tracking.

In addition, another object of the present invention is to set an image acquiring condition corresponding to luminance of the extracted characteristic point.

Further, another object of the present invention is to perform a tracking process by using a characteristic point having appropriate luminance.

Solution to Problem

In order to solve the above-mentioned problem, a fundus image acquiring apparatus of the present invention is a fundus image acquiring apparatus having a function of detecting movement of an eye to be inspected by using a characteristic image extracted from a fundus image of the eye to be inspected. The fundus image acquiring apparatus includes: fundus image acquiring unit for taking a first fundus image based on a first image acquiring condition; extraction unit for extracting a characteristic image from the first fundus image; evaluation unit for evaluating the extracted characteristic image; and setting unit for setting a second image acquiring condition based on a result of the evaluation by the evaluation unit, in which the fundus image acquiring unit takes a second fundus image based on the second image acquiring condition set by the setting unit.

Further, a control method for a fundus image acquiring apparatus according to the present invention is a control method for a fundus image acquiring apparatus having a function of detecting movement of an eye to be inspected by using a characteristic image extracted from a fundus image of the eye to be inspected. The control method includes: taking, by fundus image acquiring unit, a fundus image based on an initial image acquiring condition; extracting a characteristic image from the taken fundus image; evaluating the extracted characteristic image; and setting a new image acquiring condition based on a result of the evaluating, in which the taking includes taking, by the fundus image acquiring unit, a new fundus image.

Advantageous Effects of Invention

According to the present invention, the fundus images having sufficient luminance for tracking can be obtained.

Further features of the present invention will become apparent from the following description of exemplary embodiments with reference to the attached drawings.

DESCRIPTION OF EMBODIMENTS

Preferred embodiments of the present invention will now be described in detail in accordance with the accompanying drawings.

EXAMPLE 1

Hereinafter, Example 1 of the present invention is described.

In this example, in order to solve the problem described above, the following example is described. That is, a fundus image was obtained, and a characteristic point (also referred to as a characteristic image) was extracted. After that, luminance of the characteristic point was calculated. Thus, eye movement was able to be measured also in the case of an eye to be inspected that was not in a good condition (for example, an affected eye), by determining a fundus image obtaining condition, namely an exposure time.

(Overall Structure of Apparatus)

Figure 1:
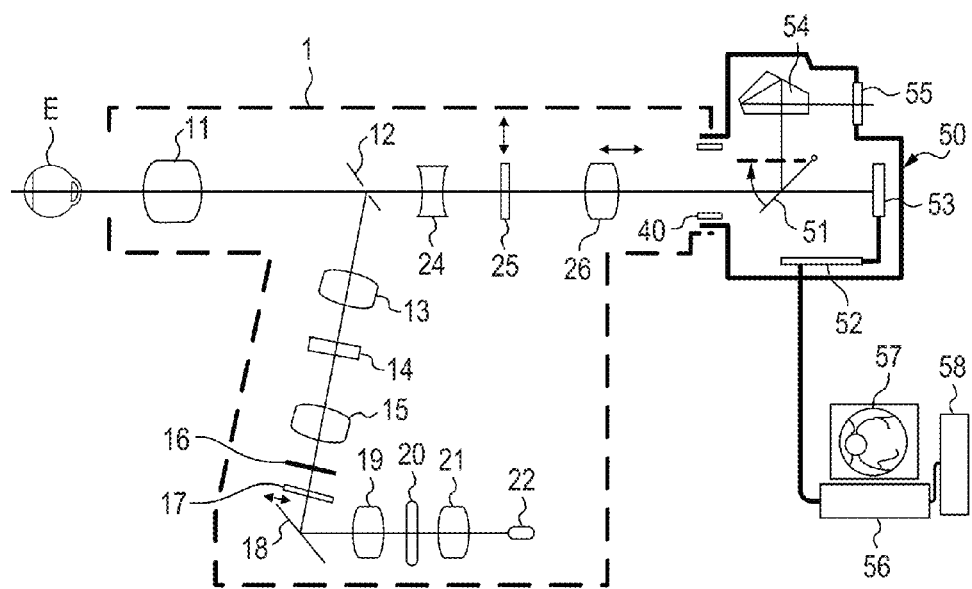
FIG. 1 is a schematic diagram illustrating a structure of an optical system of a fundus camera according to Example 1 of the present invention.

A fundus image acquiring apparatus according to this example is described with reference to FIG. 1. A fundus camera 1 is provided with a digital single-lens reflex camera 50 that can take images at a video rate, as a fundus image acquiring unit serving as a signal obtaining unit, via a connection unit 40. Using the digital single-lens reflex camera 50, the exposure time is controlled so that a fundus image obtaining rate can be controlled. A perforated mirror 12 is disposed on an optical path of an objective lens 11 that is opposed to an eye E to be inspected. On the optical path in the incident direction of the perforated mirror 12, there are arranged a relay lens 13, a black spot plate 14, a relay lens 15, a ring slit plate 16, a fluorescent exciter filter 17, and a mirror 18. Further, in the incident direction of the mirror 18, there are arranged a condenser lens 19, an imaging light source 20 constituted of a xenon tube, a condenser lens 21, and an observation light source 22 constituted of an infrared emitting diode. Note that the optical path is indicated by a solid line in the figure.

In back of the perforated mirror 12, there are arranged a focus lens 24, a fluorescent barrier filter 25, an imaging lens 26, and the digital single-lens reflex camera 50. Note that the entire fundus camera 1 is controlled by a control unit 205 (see FIG. 2, not shown in FIG. 1).

In the digital single-lens reflex camera 50, there are arranged a quick return mirror 51, a focal plane shutter (not shown), and a two-dimensional sensor 53 on the same optical path as that in the back of the objective lens 11. In addition, in the reflecting direction of the quick return mirror 51, a pentaprism 54 and an ocular lens 55 are disposed. A signal of light received by the two-dimensional sensor 53 is processed by a signal processing board 52. Then, the signal is transferred to a computer (PC) 56 via a cable and is displayed on a display 57. In addition, the PC 56 is connected to an external storage device (HDD) 58, which stores data described later.

(Functional Block)

Figure 2:
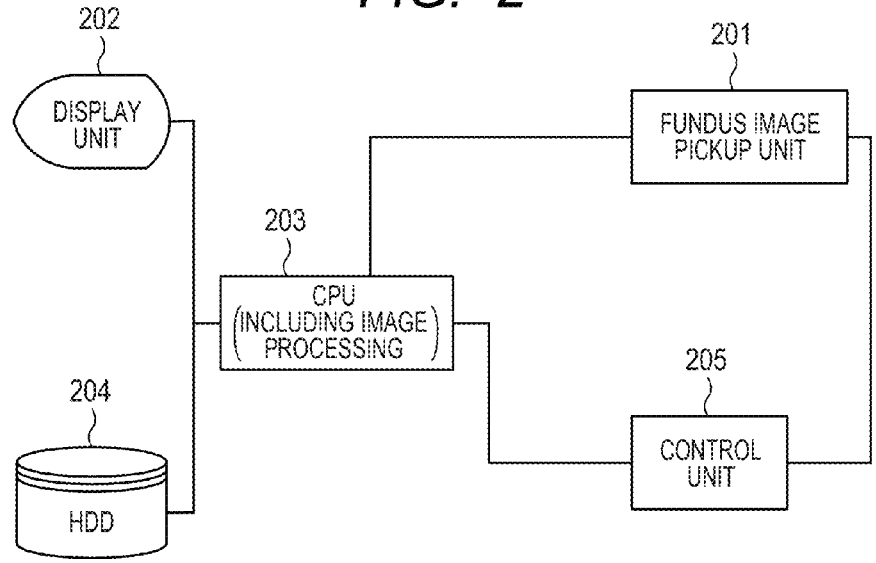
FIG. 2 is a schematic diagram of functional blocks of an apparatus according to Example 1 of the present invention.

FIG. 2 illustrates functional blocks of the fundus image acquiring apparatus according to this example. The fundus image acquiring apparatus includes a CPU 203 which controls the entire apparatus and also performs image processing and the like (corresponding to the PC 56 illustrated in FIG. 1), the control unit 205 which controls obtaining of a fundus image (inside the fundus camera 1 illustrated in FIG. 1), a fundus imaging unit 201 which takes a fundus image (fundus image acquiring unit, corresponding to the fundus camera 1 and the digital single-lens reflex camera 50 illustrated in FIG. 1), a display unit 202 which displays states of the apparatus (corresponding to the display 57 illustrated in FIG. 1), and an HDD (recording unit) 204 which records the fundus images, the image acquiring conditions, and the like (corresponding to the external storage device 58 illustrated in FIG. 1). When a fundus is observed and when an image thereof is taken, the CPU 203 issues an instruction of the image acquiring condition to the control unit 205 so that an image of the fundus is taken. After an image of the fundus is taken, the image is sent from the fundus imaging unit 201 to the CPU 203, and image processing and the like are performed. After that, the image acquiring condition is determined, and an instruction of the image acquiring condition is issued to the control unit 205 so that an image of the fundus is taken. Then, the CPU 203 analyzes the taken images so as to measure eye movement or the like, which is displayed on the display unit 202, and is stored in the recording unit 204 simultaneously or later.

(Process Flow)

Figure 3:
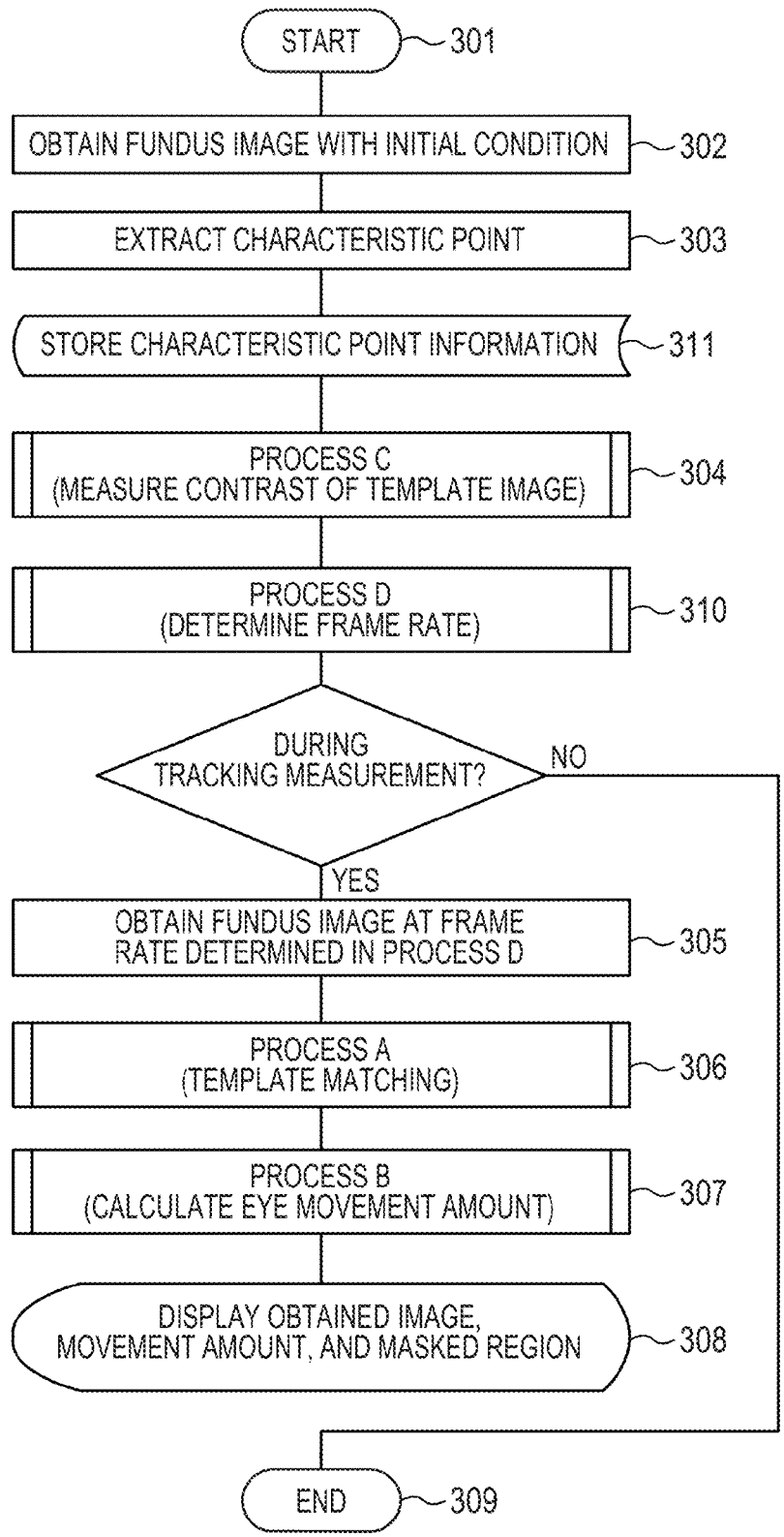
FIG. 3 is a control flow chart according to Example 1 of the present invention.

FIG. 3 illustrates a general flow of measuring eye movement for a constant period of time using the above-mentioned function.

First, the process starts by initializing the apparatus by an initial image acquiring condition (Step 301).

Next, in an imaging step, using the fundus imaging unit 201, by the initial (or first) image acquiring condition, a (first) fundus image is taken and obtained (Step 302). The initial image acquiring condition in this example includes a frame rate of 20 Hz and a fundus diameter of 10 mm. The CPU 203 extracts a characteristic point (hereinafter referred to as a template) from the obtained first fundus image (Step 303). The extraction step of extracting a characteristic point from the taken fundus image as described above is performed by a part of the CPU 203 having a function as extraction unit. Template information (template ID number, template image, coordinates (template coordinates) with respect to a reference position in the fundus image, and the like) of the extracted template is stored in the HDD 204. In this example, multiple template information pieces, preferably at least three template information pieces are stored (Step 311). After that, luminance is measured in a process C for evaluating the template image (Step 304). Luminance of the received signal is processed by 256-gradation. Based on a result of the measurement of luminance, an appropriate frame rate is calculated, and the image acquiring condition is set based on the calculated frame rate (process D) (Step 310). An image is obtained at the set frame rate, and in the obtained image (Step 305), template matching (process A) is performed (Step 306) to detect matching coordinates so that the eye movement is measured (process B) (Step 307). The eye movement amount, the image, measurement time, a real time monitor image of an anterior ocular portion, and the like are displayed on the display unit 202 (Step 308). The process from Step 305 to Step 308 is repeated until the measurement of eye movement is finished (until a new image is obtained). When an end of the measurement is instructed, the process is finished (Step 309).

Figure 4:
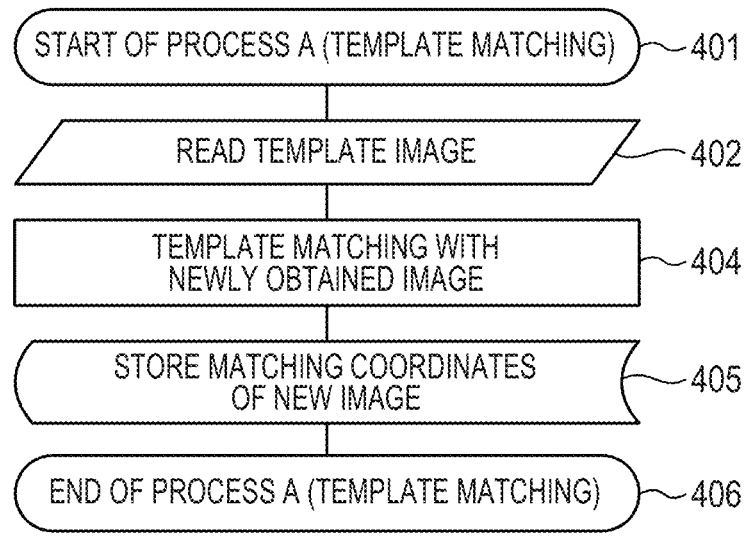
FIG. 4 is a flow chart of a process A in the control flow according to Example 1 of the present invention.

Next, the process A (Step 306) as a partial flow is described with reference to FIG. 4. As to the template matching, the template image stored in the HDD 204 is read (Step 402) so that the template matching is performed in a newly-obtained fundus image (Step 404). Because the template matching is a general process, a detailed description thereof is omitted. After the template matching is finished, coordinates obtained as a result of the matching, that is, matching coordinates are stored in the HDD 204 (Step 405). This process is performed for each template stored in the HDD 204.

Figure 5:
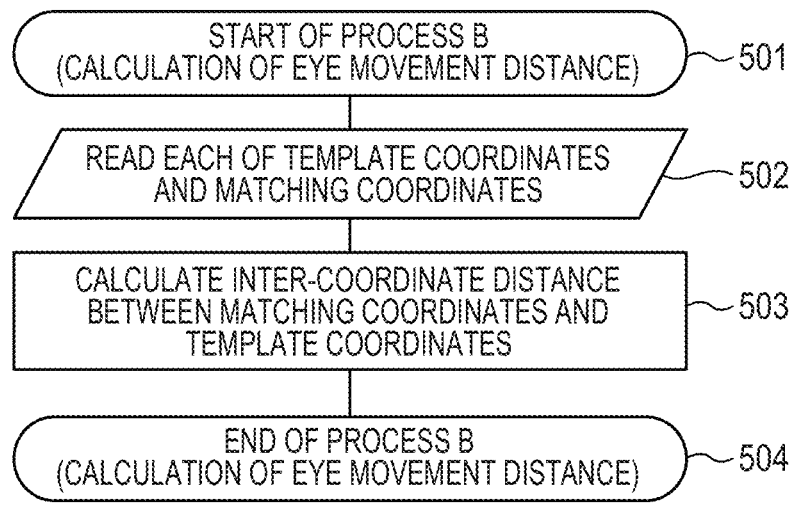
FIG. 5 is a flow chart of a process B in the control flow according to Example 1 of the present invention.

Next, the process B (Step 307) is described with reference to FIG. 5. The template coordinates and the matching coordinates are read from the HDD 204 (Step 502), and a coordinate difference is calculated for each template (Step 503) so that an eye movement distance in the fundus image is calculated from the coordinate difference.

Figure 6:
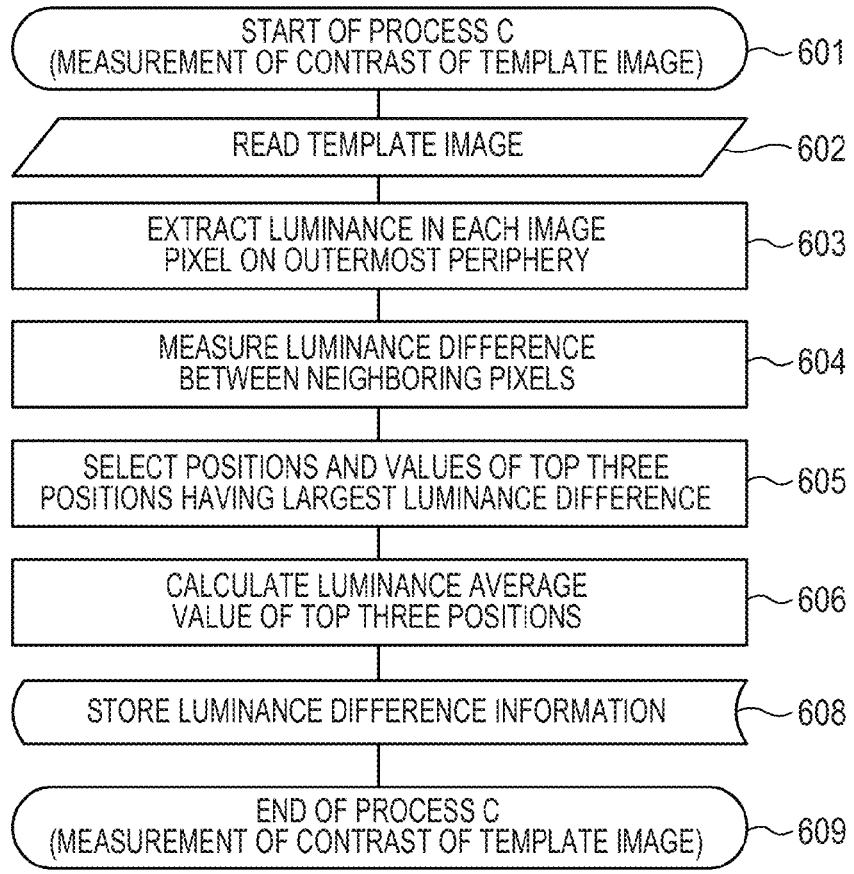
FIG. 6 is a flow chart of a process C in the control flow according to Example 1 of the present invention.

The process C (Step 304) is described with reference to FIG. 6. The obtained template image is read (Step 602). Luminance or luminance information of each pixel on the outermost periphery of the image is extracted (Step 603). A luminance difference between neighboring pixels (in the present invention, the luminance difference unit a difference in value when the signal is processed by 256-gradation) is measured (Step 604). Positions of top three spots having largest luminance differences are selected (Step 605), and a luminance difference average of the top three spots is calculated (Step 606). Luminance difference information (selected positions, luminance values of the positions, and calculated luminance difference average value) are stored in the HDD 204 (Step 608). By the above-mentioned steps, the extracted template (characteristic point) is evaluated. Therefore, the CPU 203 includes a part that functions as an evaluation unit for performing the process C based on the luminance information. A result of the evaluation by the evaluation unit is once stored in the HDD 204 as storage unit. Note that the above-mentioned process may be performed in each of the multiple extracted template images or only in a particular image, for example, in a template image that is first extracted.

Figure 7:
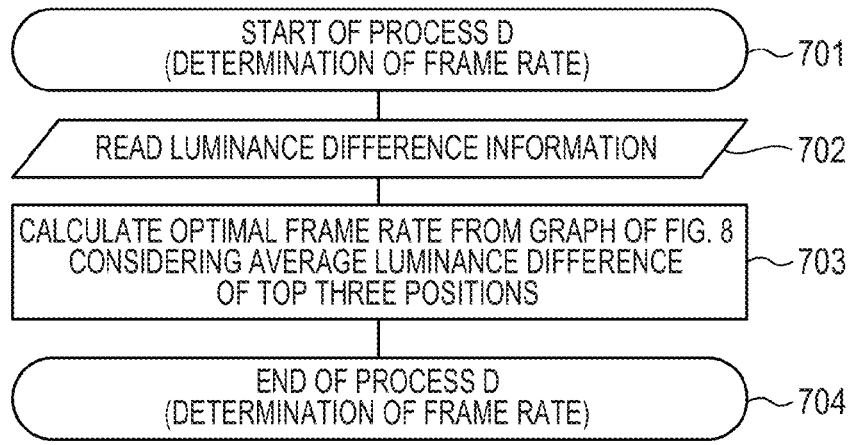
FIG. 7 is a flow chart of a process D in the control flow according to Example 1 of the present invention.
Figure 8:
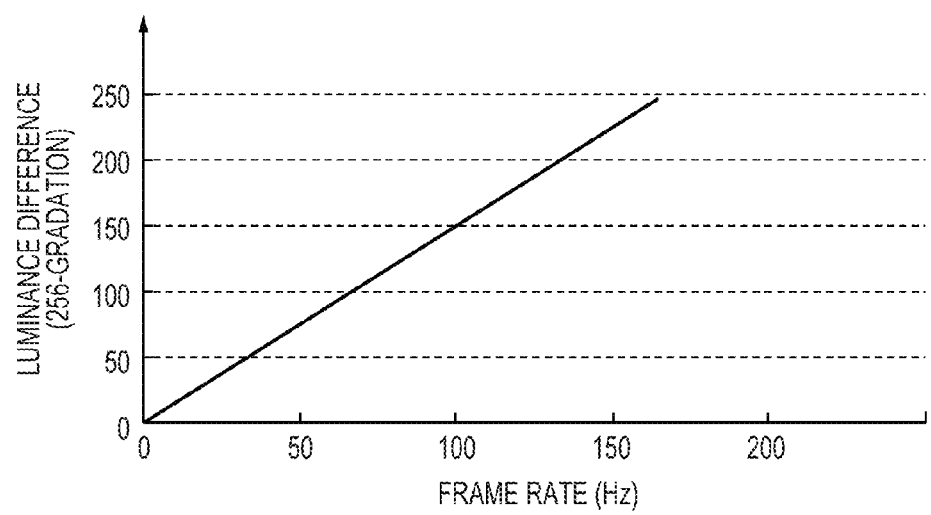
FIG. 8 is a graph showing a frame rate and a luminance difference according to Example 1 of the present invention.

The process D (Step 310) is described with reference to FIG. 7. The luminance difference information stored in the HDD 204 is read (Step 702), and a frame rate is determined based on the luminance difference information (Step 703). In other words, based on the above-mentioned result of evaluation by the evaluation unit, a new or second image acquiring condition is set. Therefore, the CPU 203 includes a part that functions as setting unit for performing the process D. As to the determination of the frame rate, for example, a table corresponding to a graph illustrated in FIG. 8 is stored in advance, and a value of the luminance difference information is associated with the table so that an appropriate frame rate is determined. The fundus imaging unit 201 as the fundus image acquiring unit takes a new (second) fundus image based on the new image acquiring condition set by the setting unit described above, and then the tracking measurement described later is performed.

Note that the above-mentioned Step 303 corresponds to the extraction step of extracting a characteristic point from the taken initial fundus image according to the present invention. In addition, the process C corresponds to an evaluation step of evaluating the extracted characteristic point, and the process D corresponds to a setting step of setting a new image acquiring condition based on a result of the evaluation by the evaluation unit. Here, the above-mentioned initial image acquiring condition for taking the first fundus image is defined as a first image acquiring condition, and the condition for taking the new or second fundus image, which is defined in the process D, is defined as a second image acquiring condition in the present invention. However, "first" and "second" in this description mean values indicating the number of times for convenience sake, and should not be interpreted to limit further setting of the number of times or the image acquiring condition. In other words, according to the number of times of the process D or repetition thereof, a newly set condition and obtained image are defined as the second condition and image, and the condition defined as the precondition and the image obtained as the precondition are defined as the first image acquiring condition and the first image, respectively.

(Tracking Measurement: Specific Example)

A specific example corresponding to the above-mentioned process is described below.

There is described a specific example in which the fundus camera 1 was used so that tracking measurement of an affected eye was performed for 20 seconds by an optical system capable of obtaining a fundus image having a fundus diameter of 10 mm.

Figure 9A:
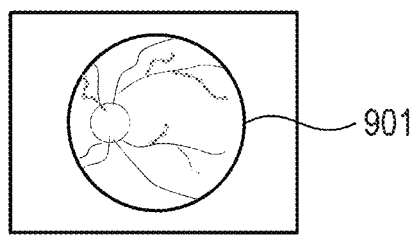
FIG. 9A is a schematic diagram illustrating a fundus image according to Example 1 of the present invention.
Figure 9B:
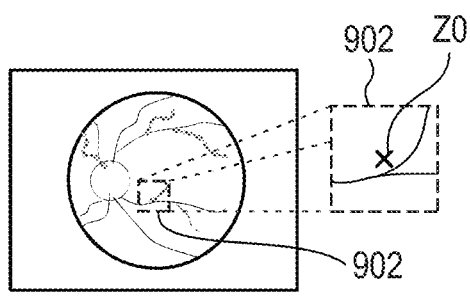
FIG. 9B is a schematic diagram illustrating a fundus image according to Example 1 of the present invention.
Figure 10:
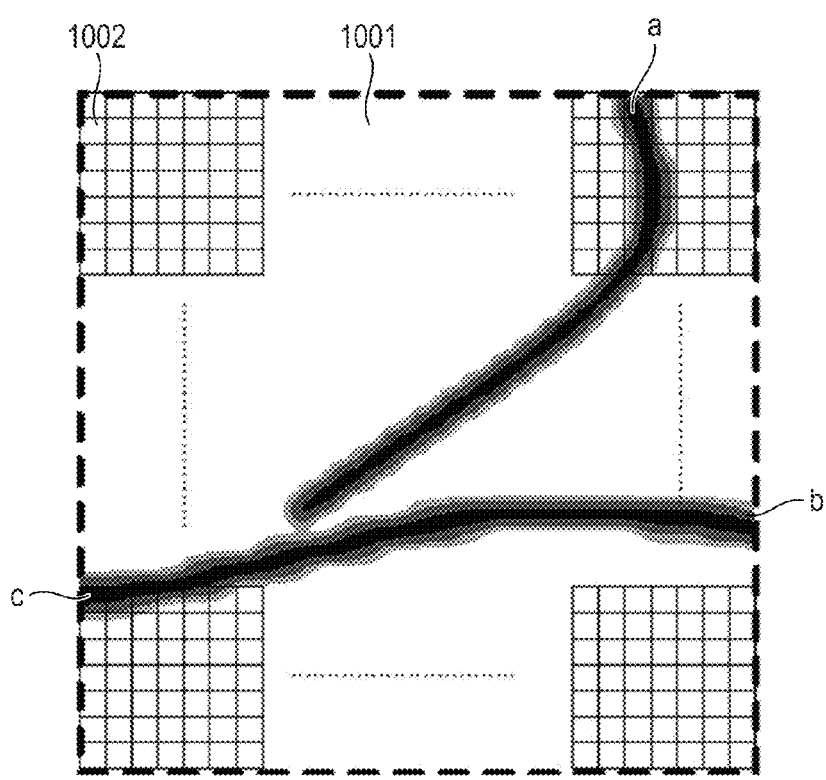
FIG. 10 is a schematic diagram of luminance difference calculation of the fundus image according to Example 1 of the present invention.

The fundus image obtained by the initial image acquiring condition is illustrated in FIG. 9A. A fundus image 901 was obtained by exposure to infrared light of 850 nm for 0.05 seconds (corresponding to a frame rate of 20 Hz). Because an affected eye was measured, a luminance difference of the fundus image was small. A template is extracted from the fundus image 901. As the template, a crossing of blood vessels is extracted. All the crossings of blood vessels are extracted from the fundus image 901. Because the affected eye had a small luminance difference, only one spot of the template was extracted as illustrated in FIG. 9B by reference numeral 902. In the extracted template, the image luminance is evaluated. The evaluation of luminance is performed as follows. A template image 1001 is divided into multiple divided areas 1002 as illustrated in FIG. 10, and luminance of the outermost peripheral divided area 1002 is extracted. Then, a luminance difference between neighboring areas is determined. Luminance differences of three spots a, b, and c illustrated in FIG. 10 were 5, 3, and 7, respectively. An average value of the luminance differences of the three spots was 5. This luminance difference is associated with the graph illustrated in FIG. 8, and hence the appropriate frame rate of 3 Hz is determined.

Figure 9C:
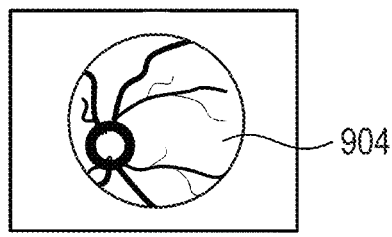
FIG. 9C is a schematic diagram illustrating a fundus image according to Example 1 of the present invention.
Figure 9D:
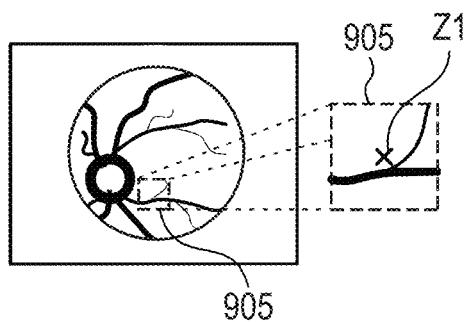
FIG. 9D is a schematic diagram illustrating a fundus image according to Example 1 of the present invention.
Figure 9E:
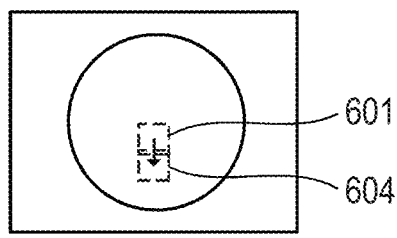
FIG. 9E is a schematic diagram illustrating a fundus image according to Example 1 of the present invention.

The fundus image obtained when the frame rate is set to 3 Hz is illustrated in FIG. 9C. In a newly-obtained fundus image 904, luminance was secured that enabled the template matching, because the frame rate was decreased. The template matching is performed in the fundus image 904 so that a matching image 905 is detected. Template coordinates Z0 are determined from FIG. 9B, matching coordinates Z1 are determined from FIG. 9D, and a variation is determined from the respective sets of coordinates so that an eye movement amount is calculated. The CPU 203 includes a part that functions as a detection unit in the present invention, which detects a position or coordinates of a new template corresponding to the template as a characteristic point that is extracted prior to the newly-taken fundus image. The above-mentioned template matching illustrated in FIGS. 9C to 9E is repeated, so as to measure how long the eyeball has moved from the reference position during the measurement, and the above-mentioned result is displayed on a monitor in real time or after the measurement.

Here, the CPU 203 further functions as a calculation unit, so as to calculate a movement distance from the previous fundus image to the new fundus image based on the position or coordinates detected previously.

As described above, when the template matching is performed, the obtaining rate of the fundus image is optimized based on a luminance value of the template. Thus, the reliable template matching measurable even for an eye to be inspected that is not in a good condition, for example, an affected eye, can be performed.

Note that if the evaluation unit evaluates that luminance of the characteristic point is low or the luminance difference is lower than a predetermined value and hence an appropriate image cannot be obtained, the frame rate is set lower than the frame rate of the initial image acquiring condition. In addition, if it is evaluated that the luminance is high or the luminance difference is equal to or higher than the above-mentioned predetermined value, the frame rate is set higher than the frame rate of the initial image acquiring condition. In addition, the predetermined value described here unit a value related to a luminance value or a luminance difference that enables the template matching by specifying each characteristic point in the obtained template, and it is preferred that the predetermined value be set as a data table in the CPU 203 in advance together with the luminance difference to frame rate as illustrated in FIG. 8.

EXAMPLE 2

Hereinafter, Example 2 of the present invention is described.

In Example 2, the following example is described. That is, a scanning laser ophthalmoscope (SLO) was used for taking a fundus image, and eye movement was measured from the SLO fundus image in the same method as in Example 1. A result of the measurement of eye movement was fed back in real time to a fundus tomographic image acquiring apparatus (optical coherent tomography (OCT) apparatus) so that a high resolution 3D OCT image was obtained. Note that the optical path is indicated by a dot line in the figure below illustrating the apparatus structure.

(Structure of OCT Apparatus)

Figure 11:
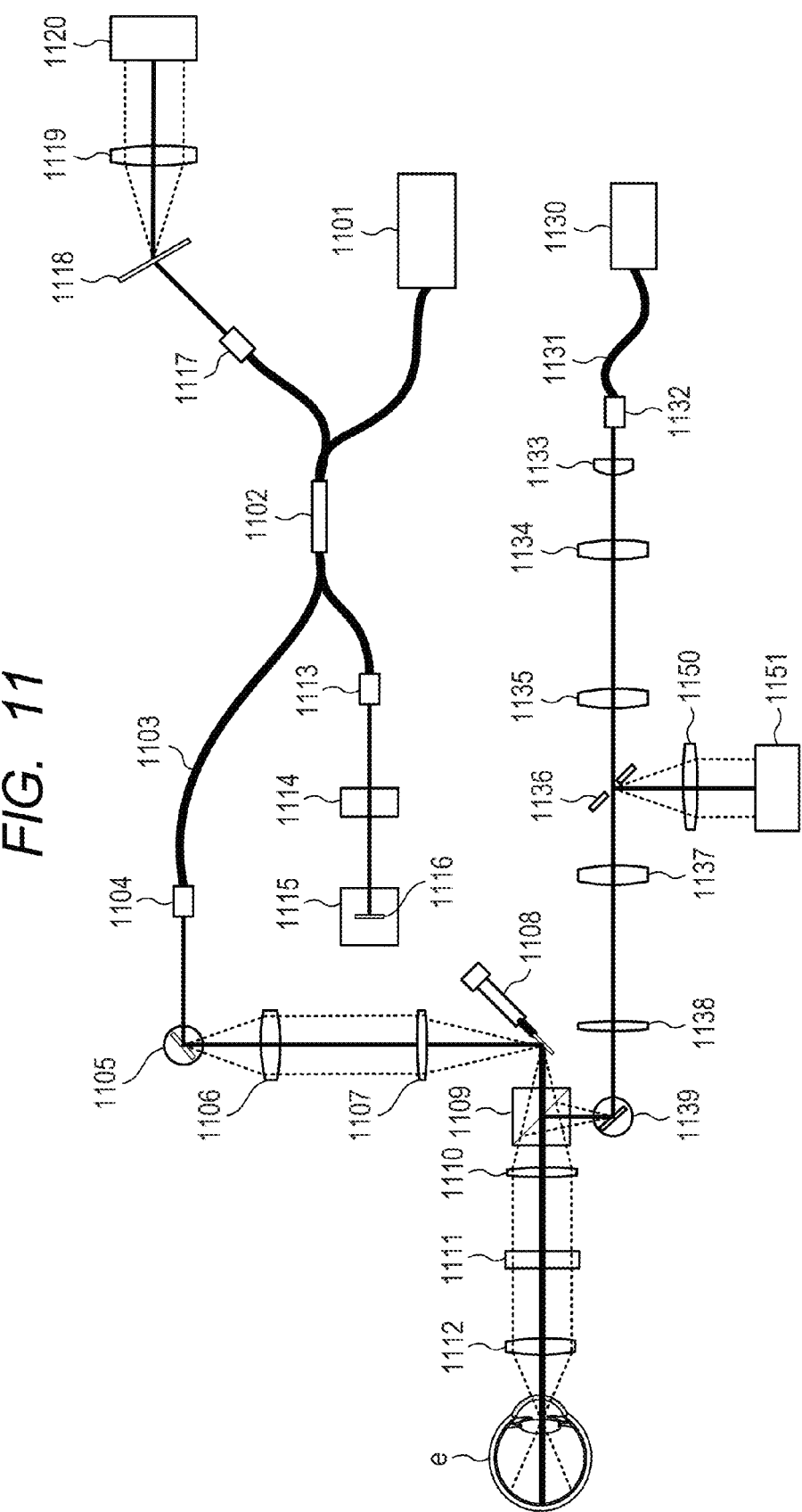
FIG. 11 is a schematic diagram illustrating a structure of an optical system of an OCT apparatus and an SLO apparatus according to Example 2 of the present invention.

An outline of the OCT apparatus is described with reference to FIG. 11.

As a low coherent light source 1101, a super luminescent diode (SLD) light source or an amplified spontaneous emission (ASE) light source can be used suitably. As a wavelength that is suitable for the low coherent light, wavelengths at 850 nm and its vicinity and at 1,050 nm and its vicinity can be used suitably for taking a fundus image. In this example, wavelengths at 850 nm and its vicinity are used. The low coherent light emitted from the low coherent light source 1101 enters a fiber coupler 1102 via a fiber and is split into a measuring beam and a reference beam. Although a structure of an interferometer using a fiber is described here, a structure using a beam splitter in a spatial light optical system may be adopted.

The measuring beam is output as a collimated beam from a fiber collimator 1104 via a fiber 1103. Further, the measuring beam passes through an OCT scanner (Y) 1105, relay lenses 1106 and 1107, an OCT scanner (X) 1108, a dichroic beam splitter 1109, a scan lens 1110, a dichroic mirror 1111, and an ocular lens 1112, so as to enter an eye e to be inspected. As the OCT scanners (X) and (Y) serving as scanning unit, a galvano scanner is used. The incident measuring beam is reflected by a retina and traces the same optical path to return to the fiber coupler 1102.

The reference beam is guided to a fiber collimator 1113 from the fiber coupler 1102 and output as a collimated beam. The output reference beam passes through a dispersion correction glass 1114 and is reflected by a reference mirror 1116 on an optical path length variable stage 1115. The reference beam reflected by the reference mirror 1116 traces the same optical path to return to the fiber coupler 1102.

The measuring beam and the reference beam that have returned are combined in the fiber coupler 1102 and guided to a fiber collimator 1117. Here, the combined light is referred to as interference light. The fiber collimator 1117, a grating 1118, a lens 1119, and a line sensor 1120 constitute a spectroscope. The spectroscope converts the interference light into intensity information of each wavelength that is measured. The intensity information of each wavelength of the interference light, which is detected by each element of the line sensor 1120, and is transmitted to a computer (not shown), in which a process is performed on the intensity information so that a tomographic image is generated.

The above-mentioned OCT apparatus corresponds to a second fundus image acquiring unit of the present invention, which functions as a tomographic image obtaining unit.

(Structure of SLO Apparatus)

Next, an optical structure of an SLO imaging unit for obtaining a fundus image is described with reference to FIG. 11 similarly.

As a laser light source 1130, a semiconductor laser or an SLD light source can be used suitably. A wavelength to be used in the light source is not limited as long as it can be separated from a wavelength of the low coherent light source for OCT by the dichroic beam splitter 1109, but a near infrared wavelength range of 700 to 1,000 nm is suitably used for image quality for observing a fundus. In this example, near infrared light of 760 nm is used as the measuring beam. The laser emitted from the laser light source 1130 is output as a collimated beam from a fiber collimator 1132 via a fiber 1131 and enters a cylindrical lens 1133. Although the cylindrical lens is used in this example, there is no particular limitation as long as the optical element can generate a line beam. A Powell lens or a line beam shaper using a diffractive optical element may be used.

The beam that is expanded by the cylindrical lens 1133 passes through the center of a ring mirror 1136 through relay lenses 1134 and 1135, and passes through relay lenses 1137 and 1138, to thereby be guided to an SLO scanner (Y) 1139. As the SLO scanner (Y) 1139, a galvano scanner is used. Further, the beam is reflected by the dichroic beam splitter 1109, and passes through the scan lens 1110 and the ocular lens 1112, so as to enter the eye e to be inspected. The dichroic beam splitter 1109 is adapted to transmit an OCT beam and to reflect an SLO beam. The beam entering the eye e to be inspected irradiates the fundus of the eye e to be inspected as a line-shaped beam. This line-shaped beam is reflected or scattered by the fundus of the eye e to be inspected and traces the same optical path so as to return to the ring mirror 1136.

The ring mirror 1136 is disposed at a position that is conjugate with a position of a pupil of the eye e to be inspected. Of the back-scattered light of the line beam irradiating the fundus, light passing through a periphery of the pupil is reflected by the ring mirror 1136 and forms an image on a line sensor 1151 by a lens 1150. The intensity information detected by each element of the line sensor 1151 is transmitted to the computer (not shown), in which a process is performed on the intensity information so that a fundus image is generated.

The SLO apparatus described above functions as a first fundus image acquiring unit for taking a fundus image for determining a frame rate in the present invention.

In this example, the SLO apparatus is described as a structure of a line scan SLO using a line beam (hereinafter referred to as an L-SLO). As a matter of course, the SLO apparatus may be a flying spot SLO. The obtaining rate of the SLO image can be changed by controlling the SLO scanner (Y) 1139.

(Functional Blocks)

Figure 12:
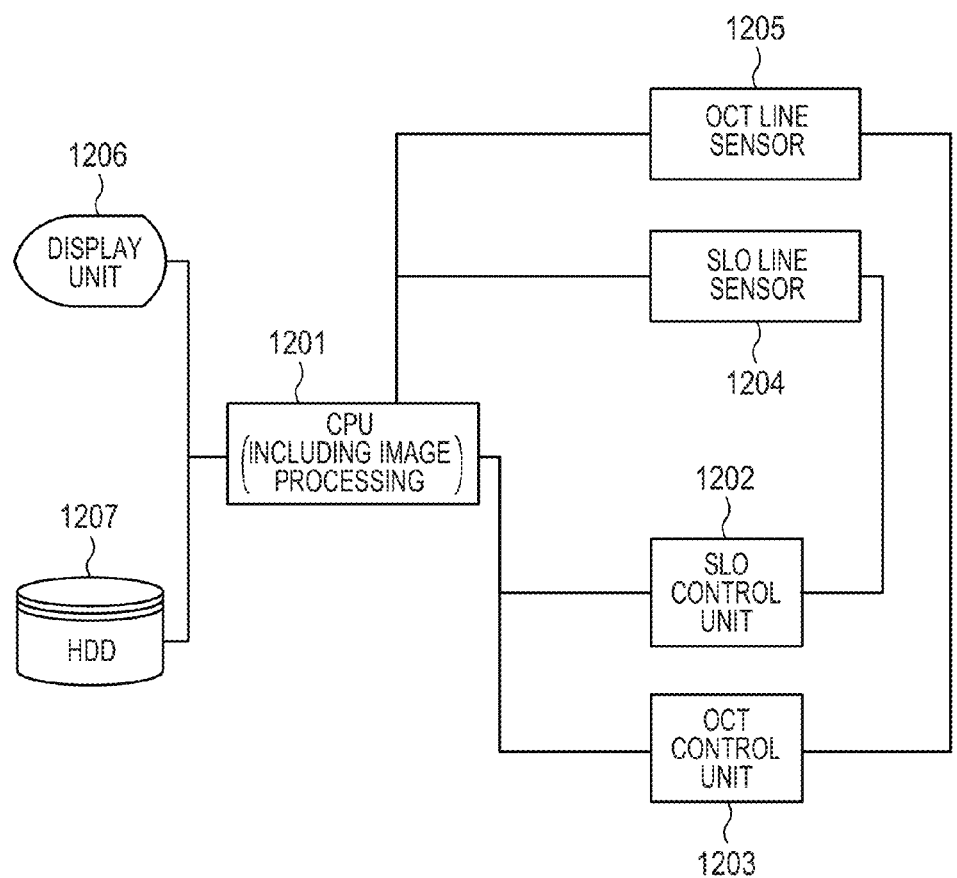
FIG. 12 is a schematic diagram of functional blocks of the apparatus according to Example 2 of the present invention.

FIG. 12 illustrates functional blocks of the system according to this example. The system includes a CPU 1201 that controls the entire system (corresponding to the above-mentioned computer), control units 1202 and 1203 that control the L-SLO and the OCT apparatus, respectively (not shown in FIG. 11), line sensors 1204 and 1205 that obtain the SLO image and the OCT image, respectively (corresponding to 1151 and 1120 illustrated in FIG. 11), a display unit 1206 that displays states of the system (not shown in FIG. 11), and a recording unit 1207 that records the fundus image, the image acquiring condition, and the like (hereinafter referred to as HDD, not shown in FIG. 11). When a fundus image is taken, the CPU 1201 issues instructions of the image acquiring condition to the control units 1202 and 1203 so that a fundus image is taken. After a fundus image is taken, the line sensors 1204 and 1205 send image signals to the CPU 1201, and image processing is performed. After that, the fundus image is displayed on the display unit 1206, and is stored in the HDD 1207 simultaneously or later.

(Process Flow)

Figure 13:
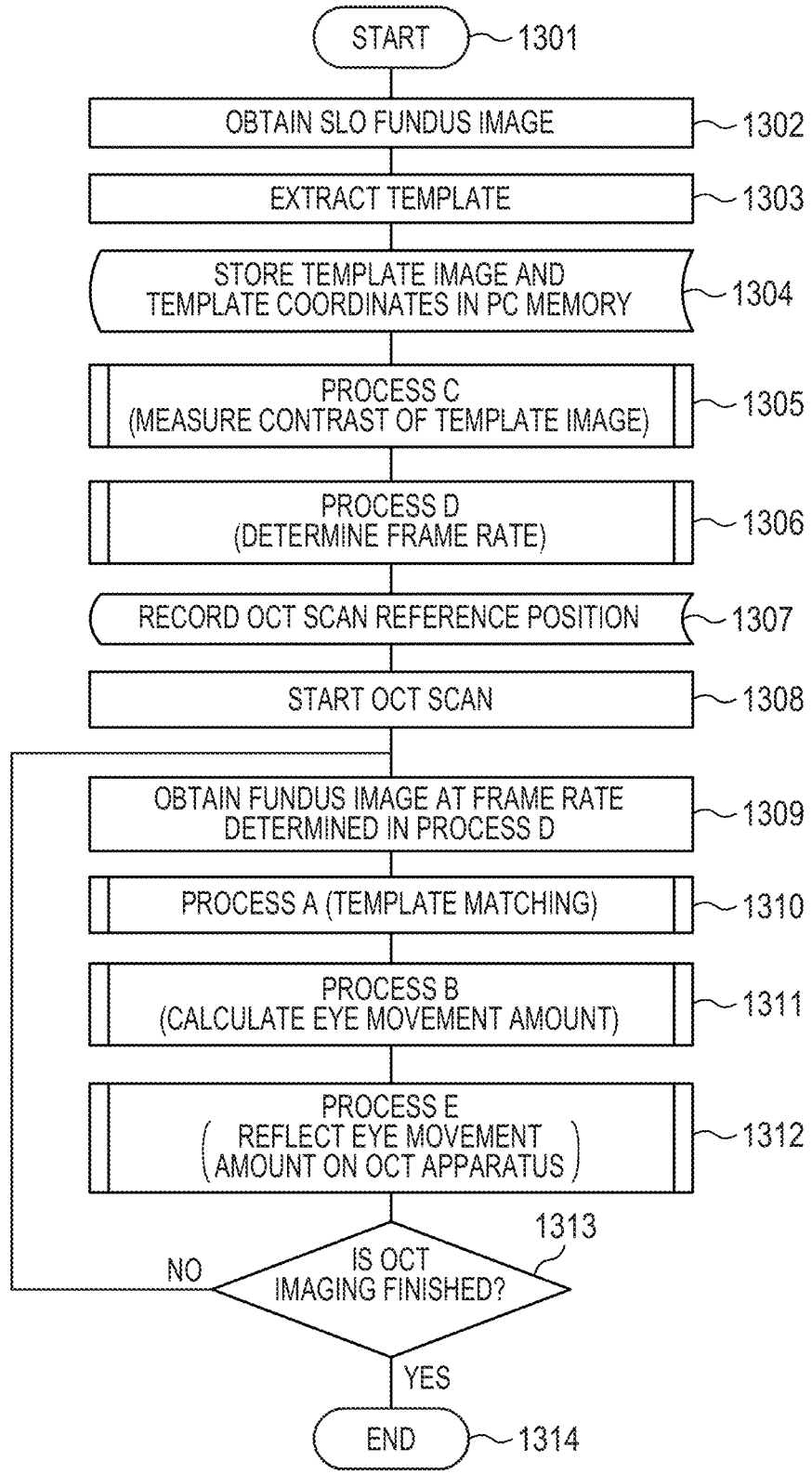
FIG. 13 is a control flow chart according to Example 2 of the present invention.

FIG. 13 illustrates a general flow of measuring eye movement during the period while the OCT apparatus is taking a tomographic image of the eyeball using the above-mentioned function. Note that in the following description, the same process as in Example 1 is described briefly.

The SLO apparatus is activated so that a fundus image (SLO image) is obtained (Step 1302). A template is extracted from the SLO image (Step 1303). After the template is extracted, an image and coordinates of the template information are stored (Step 1304). Similarly to Example 1, luminance of the template image is measured (Step 1305). An appropriate frame rate is calculated from the luminance (Step 1306). Note that a frame rate for the SLO image and a frame rate for the OCT image have data compatibility recorded in advance, and hence this compatibility is reflected on setting of the frame rate. A scan reference position of the OCT apparatus is recorded (Step 1307), and the measurement by the OCT apparatus is started (Step 1308). An OCT image is obtained at the frame rate determined in the process D (Step 1309). After that, the process A (template matching) (Step 1310) and the process B (calculation of eye movement amount) (Step 1311) are performed, a process E (feedback to the OCT apparatus) is performed (Step 1312), and Steps 1309 to 1313 are repeated for the period while the OCT apparatus is measuring the tomographic image continuously. After the OCT imaging is finished, the measurement of eye movement is finished (Step 1314).

In this example, the CPU 1201 performs the process B as the calculation unit so as to calculate the eye movement amount. The OCT control unit 1203 corrects scan positions and conditions such as scan positions of the OCT scanner (Y) 1105 and the OCT scanner (X) 1108 as the scanning unit based on the calculated eye movement amount. The CPU 1203 includes a part that functions as correction unit for performing such correction.

Figure 15:
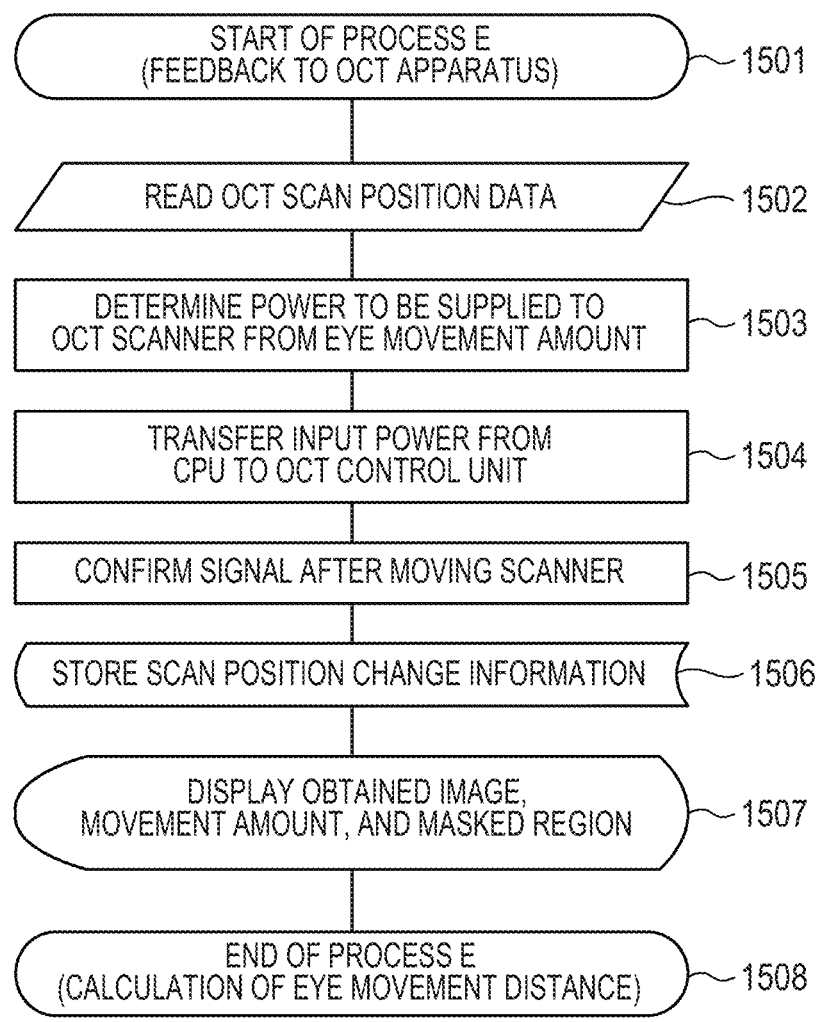
FIG. 15 is a flow chart of a process E in the control flow according to Example 2 of the present invention.

The process E (Step 1312) (feedback to the OCT apparatus) is described with reference to FIG. 15. The CPU 1201 reads the scan position data of the OCT apparatus (Step 1502), and calculates voltages to be applied to the OCT scanners 1105 and 1108 from the eye movement amount (Step 1503). After the CPU 1201 transfers the input power to the OCT control unit 1203 (Step 1504), a signal indicating movement of the scanners is confirmed (Step 1505). Then, change information of the scan positions (information for correcting the scan positions based on the eye movement amount) is stored (Step 1506). The changed state, the OCT image, the SLO image (display of the matching region and the template position), remaining time, and the like are displayed (Step 1507).

(Tracking Measurement: Specific Example)

A specific example corresponding to the above-mentioned process is described below.

An image of fundus of 10 mm×8 mm is taken by the L-SLO, and the tracking measurement is performed for 20 seconds. The OCT apparatus controls the camera to work at 70 k A-scan, the B-scan image (fundus scan range of 10 mm and a laser spot diameter of 20 μm) is constituted of 1,000 lines, and 280 B-scan images and 3D images of the retina are obtained. The measurement time is 4 seconds.

Figure 16A:
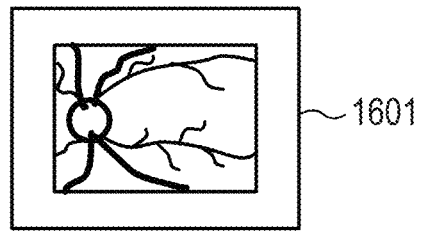
FIG. 16A is a schematic diagram illustrating an SLO fundus image according to Example 2 of the present invention.
Figure 16B:
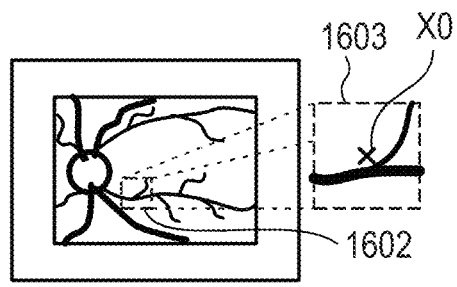
FIG. 16B is a schematic diagram illustrating an SLO fundus image according to Example 2 of the present invention.
Figure 16C:
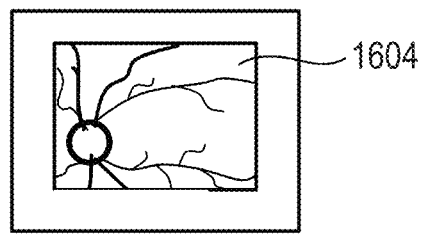
FIG. 16C is a schematic diagram illustrating an SLO fundus image according to Example 2 of the present invention.
Figure 16D:
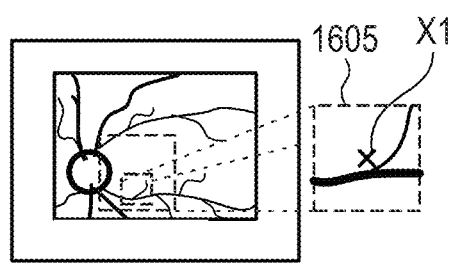
FIG. 16D is a schematic diagram illustrating an SLO fundus image according to Example 2 of the present invention.
Figure 16E:
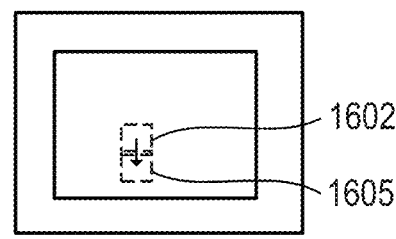
FIG. 16E is a schematic diagram illustrating an SLO fundus image according to Example 2 of the present invention.

FIG. 16A illustrates an SLO image 1601 obtained by the L-SLO. In the SLO image 1601, as illustrated in FIG. 16A, blood vessels extend from the optic papilla to the edge part in a complex manner. After the SLO image 1601 is obtained, the template image is extracted from the SLO image 1601 (1603 illustrated in FIG. 16B). The template image 1603 and template coordinates X0 (−25, −200) are stored. The origin (0, 0) of the coordinates is the center of the SLO image 1601. The luminance difference of the template image 1603 is measured. A value of the average luminance difference in this example is 100. As understood from FIG. 8, an appropriate frame rate of the luminance value of 100 is 70 Hz. FIG. 16C illustrates an SLO image 1604 obtained at the frame rate of 70 Hz. Using the SLO image 1604, the template matching is performed. The result is illustrated in FIG. 16D. After a matching image 1605 is detected, coordinates X1 (−25, −250) of the matching image 1605 are stored. After that, as illustrated in FIG. 16E, an eye movement amount (movement distance) is calculated from a coordinate difference between the template image 1603 and the matching image 1605.

Figure 14:
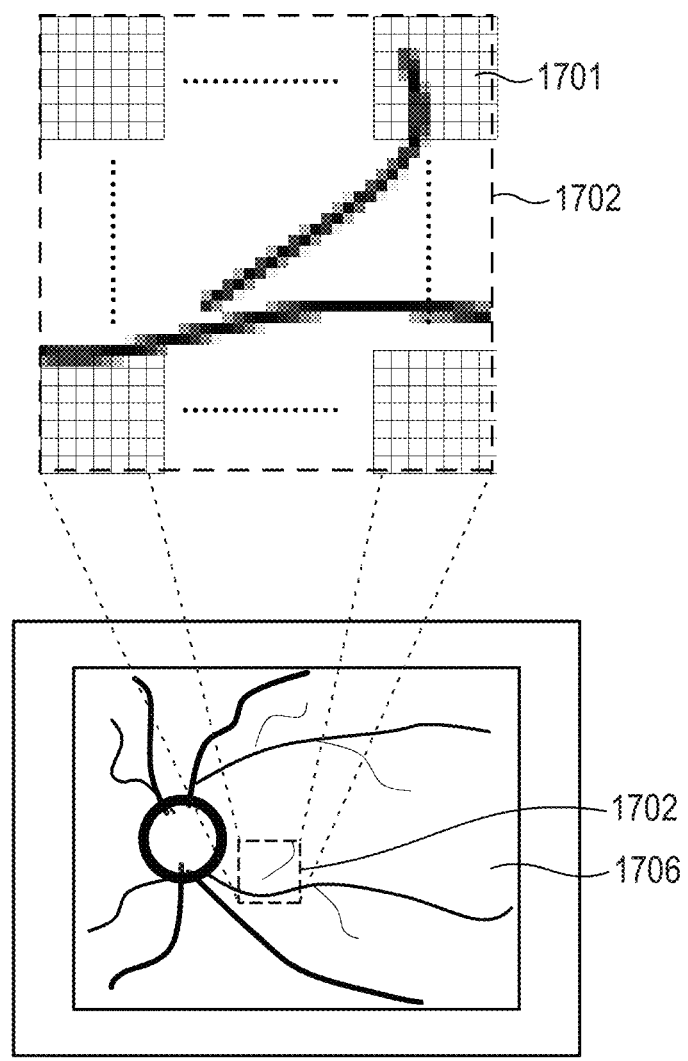
FIG. 14 is a schematic diagram of luminance difference calculation of a fundus image according to Example 2 of the present invention.

Measurement of luminance of the template image is described with reference to FIG. 14. A template image 1702 is extracted from an obtained SLO image 1706. The extracted template image 1702 is divided by a pitch of 10 μm indicated by 1701. Luminance of each divided area is measured. A sum of luminance values of three pitch areas at the image end portion is calculated, and a luminance difference of neighboring three pitch areas is calculated. An average luminance difference of ten spots having large luminance differences is calculated.

The display unit 1206 displays an SLO image obtaining rate, an OCT image, an eye movement measurement result, remaining measurement time, the image acquiring condition, and the like, and hence the user can confirm the operation.

As described above, the frame rate for obtaining the fundus images is determined from the luminance value of the template image. Thus, it is possible to increase speed of measurement of eye movement, and a higher resolution 3D retina tomographic image can be obtained by reflecting the eye movement on obtaining the OCT image.

Other Examples

In Examples 1 and 2, the template of blood vessels is extracted, but the same effect can be obtained by extracting a template of a macula lutea or a papilla. The fundus camera and the SLO apparatus are used for obtaining the fundus images, but another apparatus may be used for obtaining the fundus images. Even if the order of the steps in the flow are different from that described in the examples, or if another flow is used, the same effect can be obtained by determining the frame rate for obtaining the fundus images based on luminance of the template.

In the above-mentioned examples, after determining the frame rate, the initial template image is used for performing template matching between images obtained at different frame rates. However, the template may be extracted again after the frame rate is determined, and the template image after determining the frame rate may be used for performing the template matching between images obtained at the same frame rate.

In the method of calculating the template luminance, the graph illustrated in FIG. 8 is used. However, the graph to be used may be changed based on other attribution information, so as to calculate the frame rate with higher accuracy. Thus, a further effect can be expected. Further, the dividing method as illustrated in FIGS. 10 and 14 is used for selecting luminance of the template image, but another method of calculating luminance may be adopted. In addition, when performing reexamination of the same subject, a more accurate matching region can be set by using the image data (in particular, frame rate) of the previous measurement. The same effect can be obtained by using an SN ratio as the luminance information of the template.

The OCT apparatus is used in Example 2, but the same effect can be confirmed by using an ophthalmologic apparatus for a vision field test or the like. In addition, eye movement correction is performed in real time for the ophthalmologic apparatus, but the effect can be obtained also by performing the correction or post-measurement process after the measurement is finished.

In addition, the present invention is realized also by performing the following process. That is, software (program) for realizing the above-mentioned functions of the examples is supplied to the system or the apparatus via a network or various types of storage media, and the computer (CPU or MPU) of the system or the apparatus reads and executes the program.

REFERENCE SIGNS LIST

1: fundus camera
50: digital single-lens reflex camera

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-137945, filed Jun. 17, 2011, which is hereby incorporated by reference herein in its entirety.

The invention claimed is:

1. A fundus image acquiring apparatus, comprising:
a first fundus image acquiring unit configured to acquire, at a first frame rate, a first fundus image including at least one fundus image of an eye to be inspected;
an extraction unit configured to extract a characteristic image including a characteristic point from the acquired first fundus image;
an evaluation unit configured to evaluate luminance of the characteristic image for detecting a movement of the eye to be inspected;
a determination unit configured to determine a second frame rate based on a result of the evaluation by the evaluation unit;
a second fundus image acquiring unit configured to acquire, at the second frame rate, a second fundus image including the characteristic point, wherein luminance of the acquired second fundus image is different from luminance of the acquired first fundus image; and
a detection unit configured to detect the movement of the eye to be inspected based on the acquired second fundus image,
wherein the determination unit determines the second frame rate on the basis of a luminance difference between luminance information of each of a plurality of divided areas in the extracted characteristic image,
wherein the first fundus image acquiring unit uses an image sensor to acquire the first fundus image,
wherein the second fundus image acquiring unit uses an image sensor to acquire the second fundus image, and
wherein the extraction unit, the evaluation unit, the determination unit, and the detection unit are implemented using a processor.

2. A fundus image acquiring apparatus according to claim 1, wherein the second frame rate is determined to be lower than the first frame rate in a case where the luminance of the characteristic image is lower than a predetermined value.

3. A fundus image acquiring apparatus according to claim 1, wherein the second frame rate is determined to be higher than the first frame rate in a case where the luminance of the characteristic image is higher than the predetermined value.

4. A fundus image acquiring apparatus according to claim 1, wherein the extraction unit extracts at least three characteristic images from the acquired second fundus image, and
wherein the detection unit detects the movement based on the at least three characteristic images.

5. A fundus image acquiring apparatus according to claim 4, further comprising:
  a tomographic image obtaining unit configured to obtain a tomographic image of the eye to be inspected by using a scanning unit;
  a calculation unit configured to calculate a movement amount of the acquired second fundus image based on the at least three characteristic images; and
  a correction unit configured to correct a scanning position of the scanning unit based on the calculated movement amount,
  wherein the tomographic image obtaining unit, the calculation unit, and the correction unit are implemented using a processor, and
  wherein the scanning unit comprises a galvano scanner.

6. A control method for controlling a fundus image acquiring apparatus, the method comprising:
  acquiring, at a first frame rate, a first fundus image including at least one fundus image of an eye to be inspected;
  extracting a characteristic image including a characteristic point from the acquired first fundus image;
  evaluating luminance of the characteristic image for detecting a movement of the eye to be inspected;
  determining a second frame rate based on a result of the evaluation by the evaluating step;
  acquiring, at the second frame rate, a second fundus image including the characteristic point, wherein luminance of the acquired second fundus image is different from luminance of the acquired first fundus image; and
  detecting the movement of the eye to be inspected based on the acquired second fundus image,
  wherein the determining step determines the second frame rate on the basis of a luminance difference between luminance information of each of a plurality of divided areas in the extracted characteristic image.

7. A control method according to claim 6, wherein the second frame rate is determined to be lower than the first frame rate in a case where the luminance of the characteristic image is lower than a predetermined value.

8. A control method according to claim 6, wherein the second frame rate is determined to be higher than the first frame rate in a case where the luminance of the characteristic image is higher than the predetermined value.

9. A control method according to claim 6, wherein the extracting step extracts at least three characteristic images from the acquired second fundus image, and
  wherein the detecting step detects the movement based on the at least three characteristic images.

10. A control method according to claim 9, further comprising:
  obtaining a tomographic image of the eye to be inspected by using a scanning unit;
  calculating a movement amount of the acquired second fundus image based on the at least three characteristic images; and
  correcting a scanning position of the scanning unit based on the calculated movement amount.

11. A non-transitory medium having stored therein a computer program configured to execute the control method according to claim 6.

12. A fundus image acquiring apparatus according to claim 1, wherein the extracted characteristic image includes a crossing of blood vessels.

13. A fundus image acquiring apparatus according to claim 1, wherein the first and second fundus images are SLO images.

* * * * *